United States Patent
Denry

(10) Patent No.: US 12,296,064 B2
(45) Date of Patent: May 13, 2025

(54) ULTRA-LIGHT WEIGHT HEMOSTATIC MICROSPHERES

(71) Applicant: University of Iowa Research Foundation, Iowa City, IA (US)

(72) Inventor: Isabelle Denry, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 155 days.

(21) Appl. No.: 17/276,396

(22) PCT Filed: Sep. 24, 2019

(86) PCT No.: PCT/US2019/052678
§ 371 (c)(1),
(2) Date: Mar. 15, 2021

(87) PCT Pub. No.: WO2020/068814
PCT Pub. Date: Apr. 2, 2020

(65) Prior Publication Data
US 2022/0040370 A1    Feb. 10, 2022

Related U.S. Application Data

(60) Provisional application No. 62/735,650, filed on Sep. 24, 2018.

(51) Int. Cl.
*A61L 24/02*    (2006.01)
*A61L 24/00*    (2006.01)

(52) U.S. Cl.
CPC ........... *A61L 24/02* (2013.01); *A61L 24/0036* (2013.01); *A61L 24/0042* (2013.01); *A61L 2400/04* (2013.01)

(58) Field of Classification Search
CPC .. A61L 24/02; A61L 24/0036; A61L 24/0042; A61L 2400/04
See application file for complete search history.

(56) References Cited

U.S. PATENT DOCUMENTS

| | | | |
|---|---|---|---|
| 8,703,634 B2 | 4/2014 | Baker et al. | |
| 9,889,154 B2 * | 2/2018 | Basadonna | ............ A61K 33/06 |
| 2009/0148502 A1 | 6/2009 | Pronovost | |
| 2013/0344131 A1 | 12/2013 | Lo et al. | |
| 2014/0308337 A1 * | 10/2014 | Baker | ..................... A61L 15/44 |
| | | | 424/443 |
| 2015/0307692 A1 * | 10/2015 | Kamal | .................... C08B 15/02 |
| | | | 536/56 |

FOREIGN PATENT DOCUMENTS

WO    WO-2020068814 A1    4/2020

OTHER PUBLICATIONS

"International Application Serial No. PCT/US2019/052678, International Search Report mailed Dec. 12, 2019", 3 pgs.

"International Application Serial No. PCT/US2019/052678, Written Opinion mailed Dec. 12, 2019", 6 pgs.

Preocanin, Tajana, et al., "Charging Behavior of Clays and Clay Minerals in Aqueous Electrolyte Solutions—Experimental Methods for Measuring the Charge and Interpreting the Results", Clays, Clay Minerals and Ceramic Materials Based on Clay Minerals, Chapter 3, (Mar. 2016), 51-88.

"International Application Serial No. PCT/US2019/052678, International Preliminary Report on Patentability mailed Apr. 1, 2021", 8 pgs.

* cited by examiner

*Primary Examiner* — Shirley V Gembeh
(74) *Attorney, Agent, or Firm* — Schwegman Lundberg & Woessner, P.A.

(57) ABSTRACT

A hemostatic composition comprises a powder of a plurality of hollow or highly-porous microparticles that exhibit hemostatic properties, wherein each of the microparticles comprise a body comprising a clay material that is a crystalline hydrated form of a layered silicate.

19 Claims, 6 Drawing Sheets

ULTRA-LIGHT WEIGHT HEMOSTATIC MICROSPHERES

CLAIM OF PRIORITY

This patent application is a U.S. National Stage Filing under 35 U.S.C. § 371 from International Application No. PCT/US2019/052678, filed Sep. 24, 2019 and published as WO 2020/068814 A1 on Apr. 2, 2020, which application claims the benefit of priority to U.S. Provisional Application Ser. No. 62/735,650, titled "ULTRA-LIGHT WEIGHT HEMOSTATIC MICROSPHERES," filed on Sep. 24, 2018, which are incorporated by reference herein in their entireties.

BACKGROUND

Hemostatic agents and devices are used to treat bleeding wounds by triggering the body's natural hemostasis response. Conventional methods of hemostasis include surgical techniques, sutures, ligatures or clips, and energy-based thermal coagulation or cauterization. When these conventional measures are ineffective, impractical, or simply unavailable, adjunctive hemostasis techniques and products are typically utilized.

A large variety of hemostatic materials has been developed and are currently available for hemorrhage control. These products include topical absorbable hemostats (TAH) such as oxidized cellulose (OC), oxidized regenerated cellulose (ORC), zeolite powder or zeolite-impregnated gauze, gelatin in various forms (with or without a thrombin solution), collagen in powder form or microfibrillar collagen, chitin, chitosan and a variety of synthetic topical sealants. To improve the hemostatic performance of these products, scaffolds can be combined with biologically-derived clotting factors, such as thrombin and fibrinogen. Although these materials exhibit some degree of success, a number of them exhibit significant drawbacks, such as difficulty in handling or removing from the wound, high cost, or undesirable side effects.

SUMMARY

The present invention is directed to a hemostatic material comprising an ultra-light weight powder of hollow or highly-porous clay microspheres. The clay microspheres have a high absorption capacity. The microspheres can be loaded with various additives, including, but not limited to, amino-acids, antimicrobial agents, hemostasis promoting agents, gelatin, collagen or combinations thereof.

In another aspect, the present invention is directed to a method of making hollow or highly-porous clay microspheres. The method, described in more detail below, includes freeze-spraying an aqueous clay suspension, followed by freeze drying to produce ultra-light weight and highly-porous microspheres with a three dimensional structure that exhibits hemostatic properties. In another aspect, the present invention is directed to a method of treating a wound by applying ultra-light weight microspheres onto a wound of a patient, or into the wound, or both.

This summary is intended to provide an overview of subject matter of the present disclosure. It is not intended to provide an exclusive or exhaustive explanation of the invention. The detailed description is included to provide further information about the present disclosure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
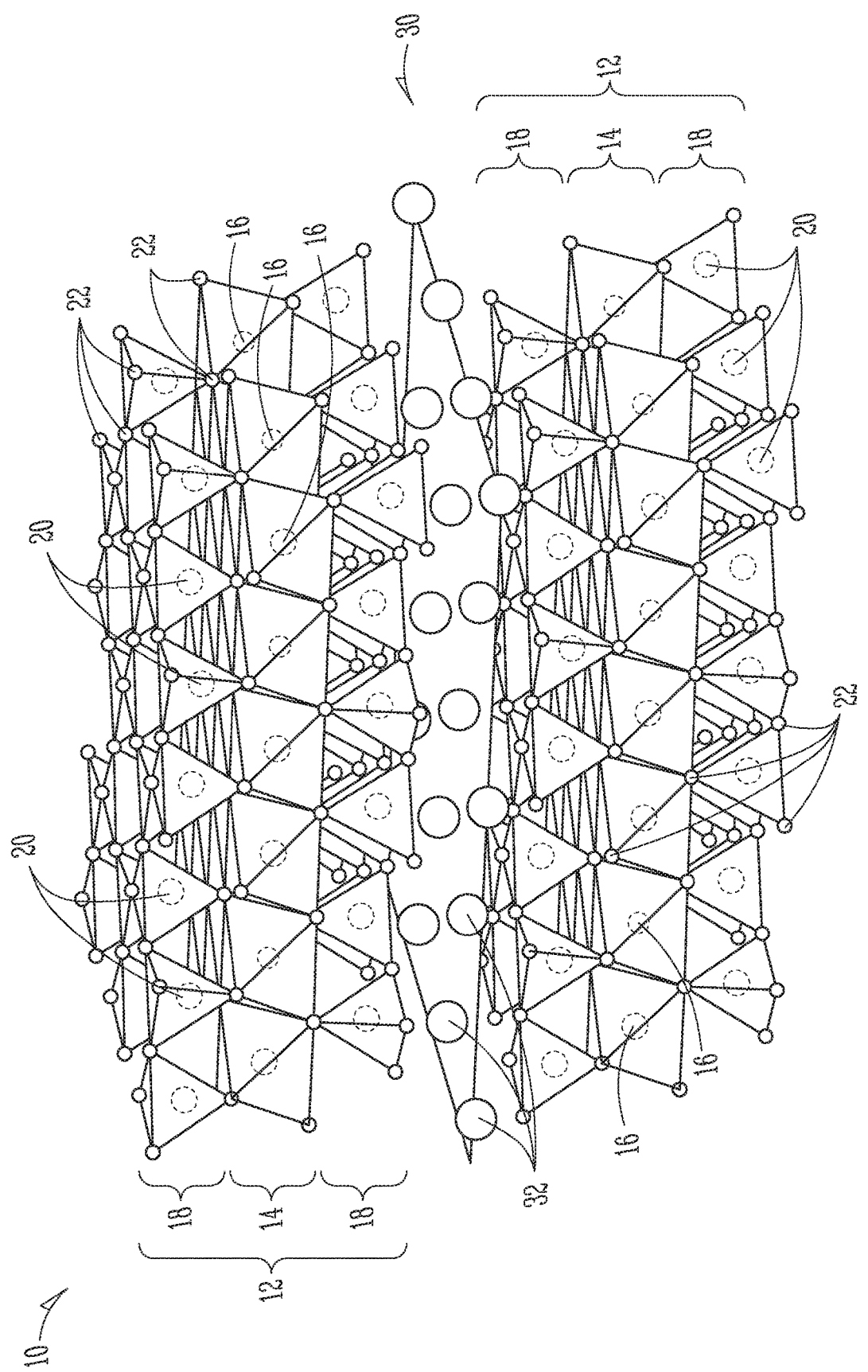
FIG. 1 is a schematic diagram of the crystallographic structure of hectorite clay, which can be used to form ultra-light weight hemostatic microparticles according to the present disclosure.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The example embodiments may be combined, other embodiments may be utilized, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

References in the specification to "one embodiment", "an embodiment," "an example embodiment," "an example," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a concentration range of "about 0.1% to about 5%" should be interpreted to include not only the explicitly recited concentration of about 0.1 wt. % to about 5 wt. %, but also the individual concentrations (e.g., 1%, 2%, 3%, and 4%) and the sub-ranges (e.g., 0.1% to 0.5%, 1.1% to 2.2%, and 3.3% to 4.4%) within the indicated range.

In this document, the terms "a" or "an" are used to include one or more than one and the term "or" is used to refer to a nonexclusive "or" unless otherwise indicated. In addition, it is to be understood that the phraseology or terminology employed herein, and not otherwise defined, is for the purpose of description only and not of limitation. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Recitation in a claim to the effect that first a step is performed, and then several other steps are subsequently performed, shall be taken to mean that the first step is performed before any of the other steps, but the other steps can be performed in any suitable sequence, unless a sequence is further recited within the other steps. For example, claim elements that recite "Step A, Step B, Step C, Step D, and Step E" shall be construed to mean step A is carried out first, step E is carried out last, and steps B, C, and D can be carried out in any sequence between steps A and E, and that the sequence still falls within the literal scope of the claimed process. A given step or sub-set of steps can also be repeated.

Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

This disclosure relates to hemostatic devices and hemostatic agents that can be applied to bleeding wounds to trigger hemostasis. The hemostatic agents comprise ultralight weight clay microparticles that are highly-porous or hollow such that the clay microspheres have a high surface area to mass ratio. As used herein, the term "microparticles" refers to a particle that has a size in its largest dimension of less than or equal to about 500 micrometers (μm), such as less than or equal to 250 for example less than or equal to about 200 In an example, the microparticles have a size in their largest direction that is from about 40 μm to about 200 and in preferred embodiments for hemostasis applications from about 50 μm to about 200 In some examples, the microparticles generally have a sphere-like or substantially sphere-like shape, such that they will also be referred to herein after as "microspheres." When the microparticles are microspheres, the size in their largest dimension can refer to the diameter of the microspheres.

In an example, the clay microspheres comprise a porous structure with a plurality of pores formed in the structure of the microsphere. In an example, the size of the pores range from about 1 μm to about 10 μm, such as from about 2 μm to about 8 μm, for example from about 3 μm to about 6 μm. In some examples, when used for hemostasis applications, the size of the pores is such that the pores are of a size that is similar to the size of blood platelets and/or that of red blood cells. Without wishing to bound by any theory, the present inventor believes that this size of pores allow the clay microspheres to incorporate not only the liquid portion of blood, but to also incorporate blood platelets and red blood cells into the clay microspheres, which can cause an increase in the local concentration of platelets or red blood cells or both, which can act as a clotting factor concentrator that leads to more rapid clot formation.

The clay microspheres exhibit hemostatic properties when placed in contact with a bleeding wound, e.g., the microspheres are capable of minimizing or stopping blood flow when placed in contact with a bleeding wound. When the clay microspheres are put into contact with a wound, then the liquid phase of blood (e.g., plasma and soluble components) is absorbed by the high-surface area clay microspheres, which facilitates clotting.

As used herein, the term "clay" refers to a crystalline hydrated form of a layered silicate. In some examples, the clay may or may not include one or more of lithium, magnesium, or sodium, aluminum, or calcium. The inventor has found that, in some examples, clay that includes hectorite has been found to be particularly useful in forming microspheres for use as a hemostatic agent.

Figure 2:
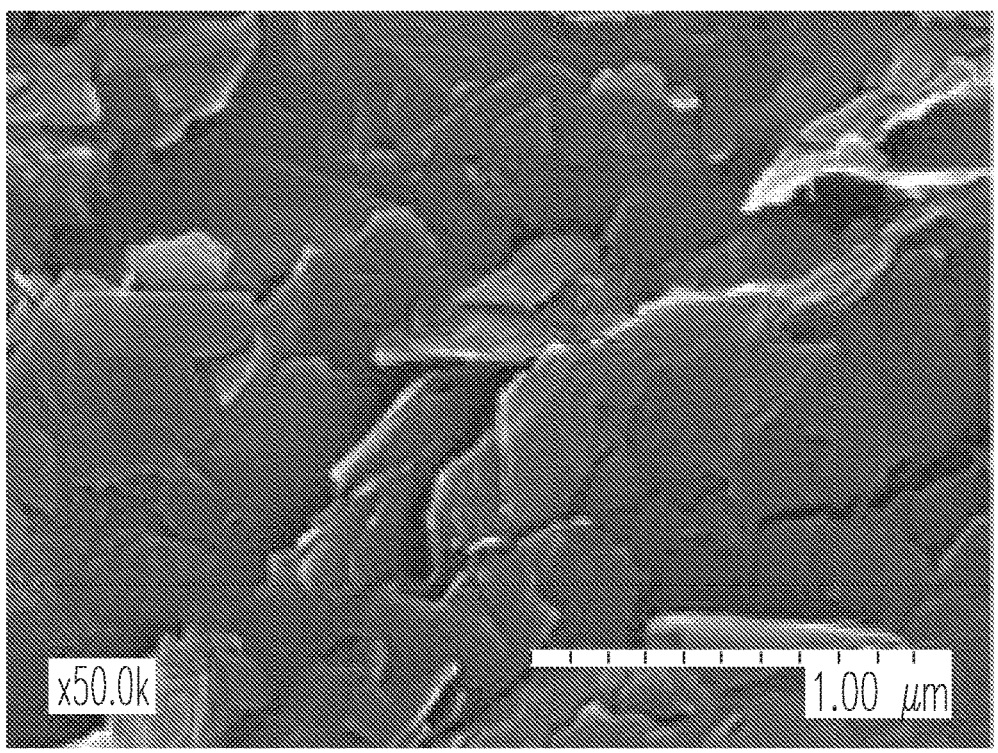
FIG. 2 is a scanning electron micrograph showing an interlocking platelet structure of hectorite clay.

Hectorite is a naturally occurring layered silicate mineral. It has the general formula $Na_{0.3}(Mg,Li)_3Si_4O_{10}(OH)_2$, and has a crystalline structure of alternating tetrahedral sheets of silicon tetrahedra and octahedral sheets of magnesium octahedra, linked via an interlayer of exchange cations such as sodium ions, lithium ions, and/or hydroxyl ions. A schematic of the hectorite crystalline structure 10 is shown in FIG. 1. As can be seen in FIG. 1, the hectorite structure 10 includes one or more layers of a sandwich substructure 12 that includes a sheet 14 of magnesium atoms 16 arranged in an octahedral pattern sandwiched between opposing sheets 18 of silicon atoms 20 arranged in a tetrahedral pattern, with linking groups 22 (e.g., oxygen atoms or hydroxyl groups) at the vertices of the octahedra of a magnesium sheet 14 and the tetrahedra of the silicon sheets 18. Between adjacent sandwich structures 12 is an interlayer 30 of ions 32. In an example, the ions 32 of the interlayer 30 are a plurality of cations 32, such as one or both of sodium ions ($Na^+$) and lithium ions ($Li^+$). Isomorphous substitutions of cations are common in clay minerals, and such substitutions often lead to a net negative charge for the structure 10, which can allow the microparticles made out of the clay material of structure 10 to be a surface-charge activator of clotting factors XI and XII. In some examples, the cationic interlayer 30 can be intercalated with therapeutic agents or amino acids so that the clay material can act as a carrier of one or more wound-healing promoter compounds. The layered structure 10 of hectorite often takes the form of interlocked platelets, as is shown on the scanning electron micrograph (SEM) shown in FIG. 2. In some examples, these platelets are nanoscale sized platelets that collectively form the overall hectorite structure.

While the present disclosure describes the use of hectorite to form the clay microspheres, other clay minerals can also be used without varying from the scope of the present invention. Examples of other clay materials that can be used to form the clay microspheres, either in addition to or in place of hectorite, include, but are not limited to, laponite, kaolinite, bentonite, montmorillonite, saponite, hectorite, palygorskite, sepiolite or combinations thereof.

Figure 3:
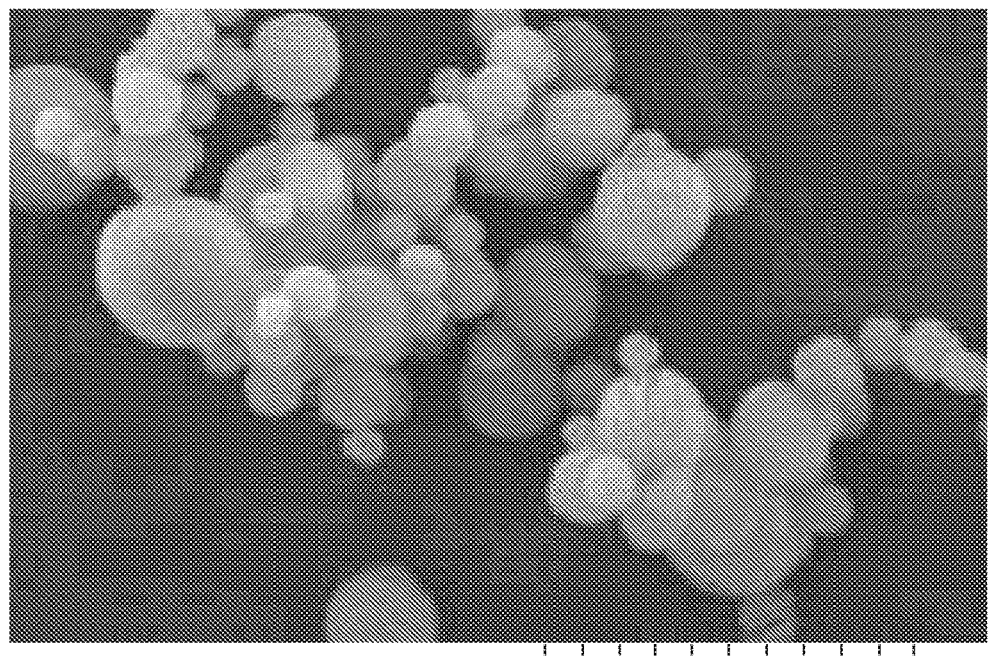
FIG. 3 is a scanning electron micrograph of the ultra-light weight hemostatic clay microparticles described herein.
Figure 4:
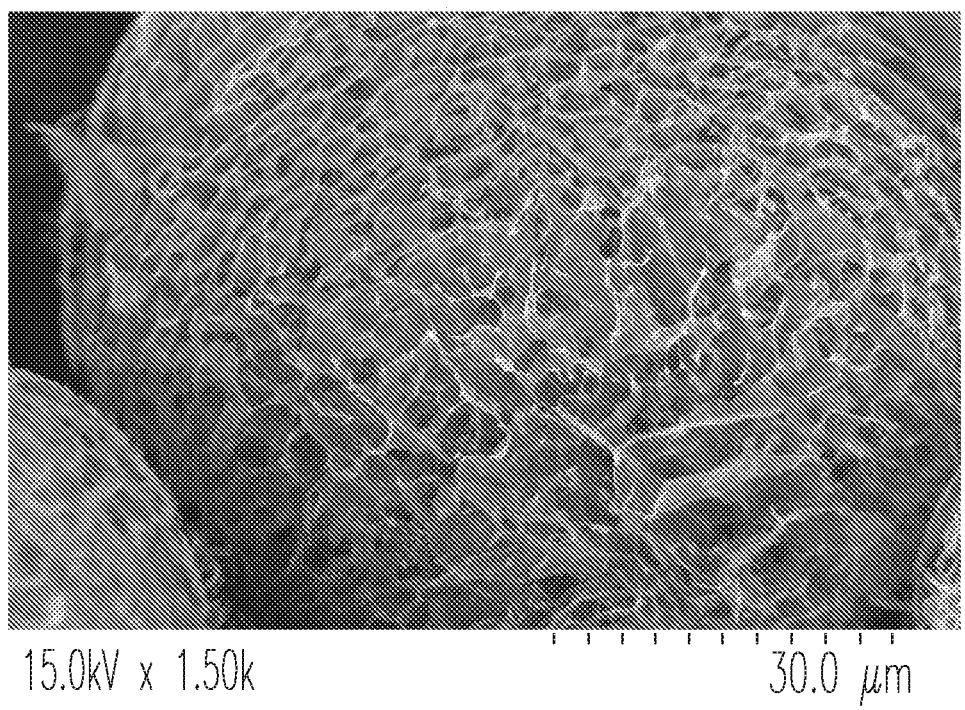
FIG. 4 is a scanning electron micrograph the same ultra-light weight hemostatic clay microparticles shown in FIG. 3 at a higher magnification.

In an example, the clay microspheres have a three dimensional structure that resembles the so-called "desert rose" crystal formation of gypsum or barite mineral, as shown in the SEM images of FIGS. 3 and 4. As can be seen in FIGS. 3 and 4, the microsphere structure includes a large number of pores and a large porous network, resulting in a very high specific surface area for the microspheres, e.g., a specific surface area of at least about 75 square meters per gram ($m^2/g$), for example at least about 80 $m^2/g$, such as at least about 90 $m^2/g$, for example at least about 95 $m^2/g$, such as at least about 100 $m^2/g$, for example at least about 105 $m^2/g$, such as at least about 110 $m^2/g$. In an example, the density of uncompacted clay microsphere powder is from about 0.006 $g/cm^3$ to about 0.009 $g/cm^3$ (for hectorite microspheres).

Figures 5A, 5B, 5C:
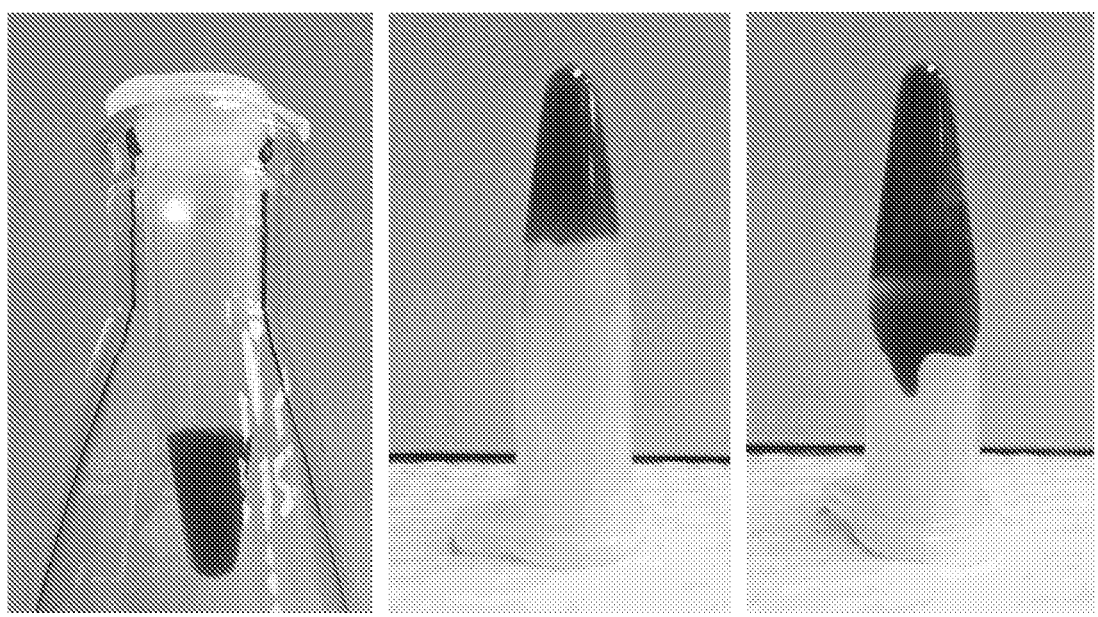
FIGS. 5A-5C are pictures showing the clotting of a sample of citrated bovine blood before (A) and after being mixed with the ultra-light weight hemostatic clay microparticles described herein (B) or after being mixed with commercially available topical hemostatic agent (Gelfoam®).

The clay microspheres described herein are biocompatible and in some examples is bioresorbable, which is particularly useful for hemostasis applications. The hemostatic powder can be applied directly to the wound, such as with a bellows applicator or placed in a biodegradable compress pouch to conform to the wound and for easy handling. FIGS. 5A-5C show the ability of the microsphere powder to enable rapid blood clotting. FIG. 5A is a picture of 0.2 milliliters (mL) of citrated bovine blood in an Eppendorf tube. FIG. 5B is a picture of the same tube after adding 10 milligrams (mg) of hectorite microspheres to the citrated bovine blood and the mixture was swirled and allowed to sit for 60 seconds, the tube was then turned upside down. FIG. 5C is a picture of an Eppendorf tube after adding 10 milligrams (mg) of commercially available topical hemostatic agent Gelfoam® to 0.2 milliliters (mL) of citrated bovine blood, the mixture was swirled and the tube turned upside down. As can be seen in FIG. 5B, the blood has substantially clotted and did not flow back down the sides of the tube due to gravity, unlike in FIG. 5C with the commercially available topical hemostatic agent. The pictures of FIGS. 5A-5C demonstrate that the clay microspheres formed from the hectorite structure 10 described above have been shown to provide for blood clotting after as little as 60 seconds when used in a microsphere powder to blood ratio as low as 10 mg powder to 0.2 ml blood, even if the blood is citrated to prevent coagulation.

Figure 6:
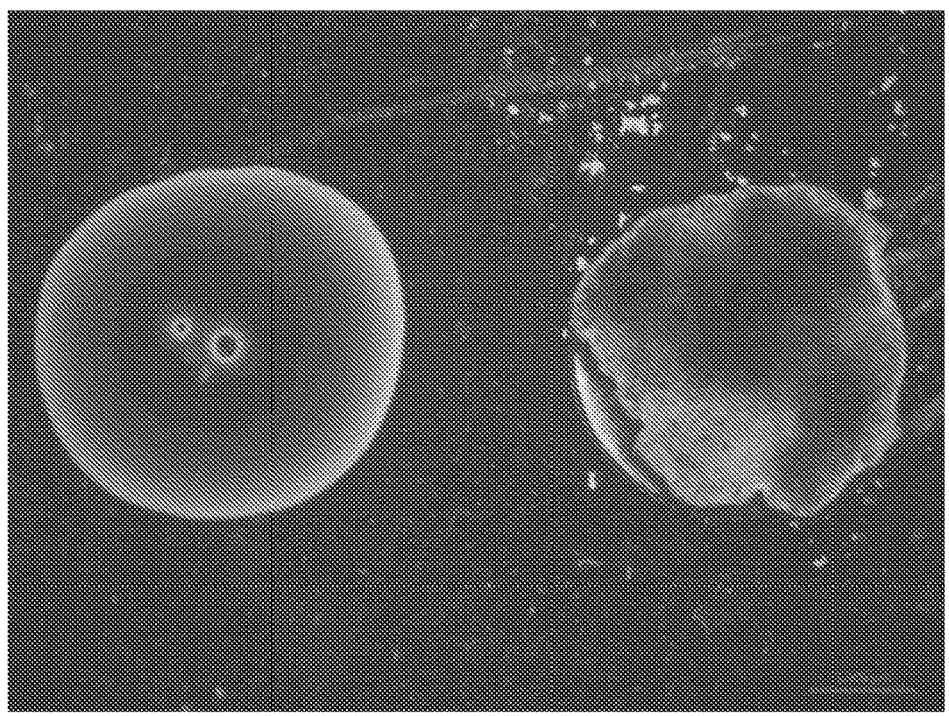
FIG. 6 is a picture of a drop of citrated bovine blood both before and after the addition of the ultra-light weight hemostatic clay microparticles described herein.

The hemostatic efficacy of the clay microspheres described herein are also illustrated in FIG. 6, which shows the effect of the clay microspheres on a single drop of citrated bovine blood. The left side of FIG. 6 shows a drop of citrated bovine blood without any of the clay microspheres added. The right side of FIG. 6 shows the drop of citrated bovine blood 60 seconds after adding some of the clay microsphere powder. As can be seen by the comparison of the left and right sides of FIG. 6, the addition of the clay microspheres caused the drop of blood to noticeably contract and to dry up as the blood clotted.

Figure 7:
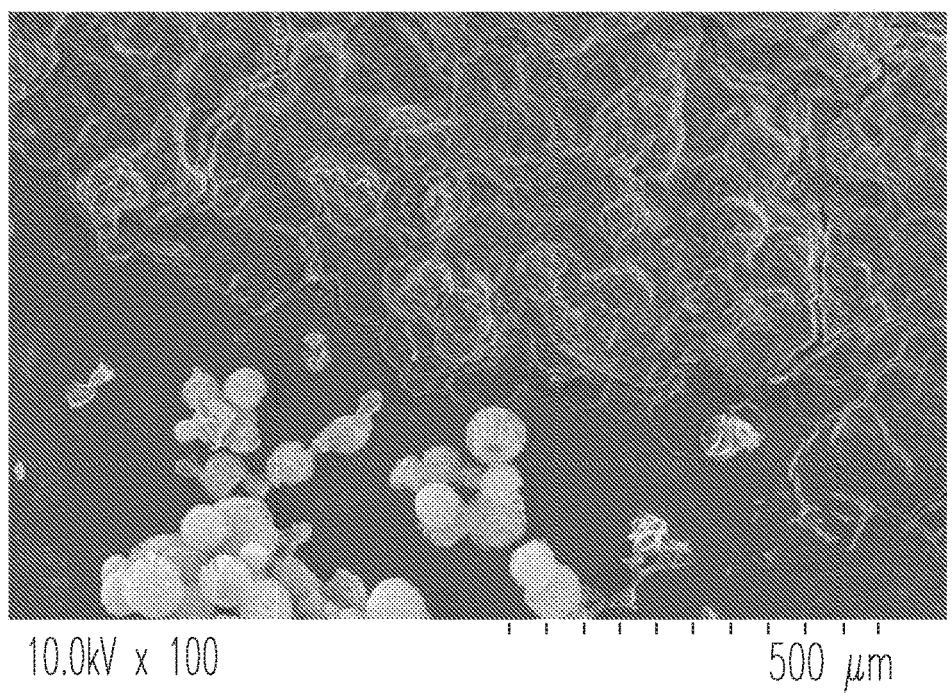
FIG. 7 is a scanning electron micrograph of several of the ultra-light weight hemostatic clay microparticles described herein that have not yet reacted with blood and several of the ultra-light weight hemostatic clay microparticles saturated with blood.
Figure 8:
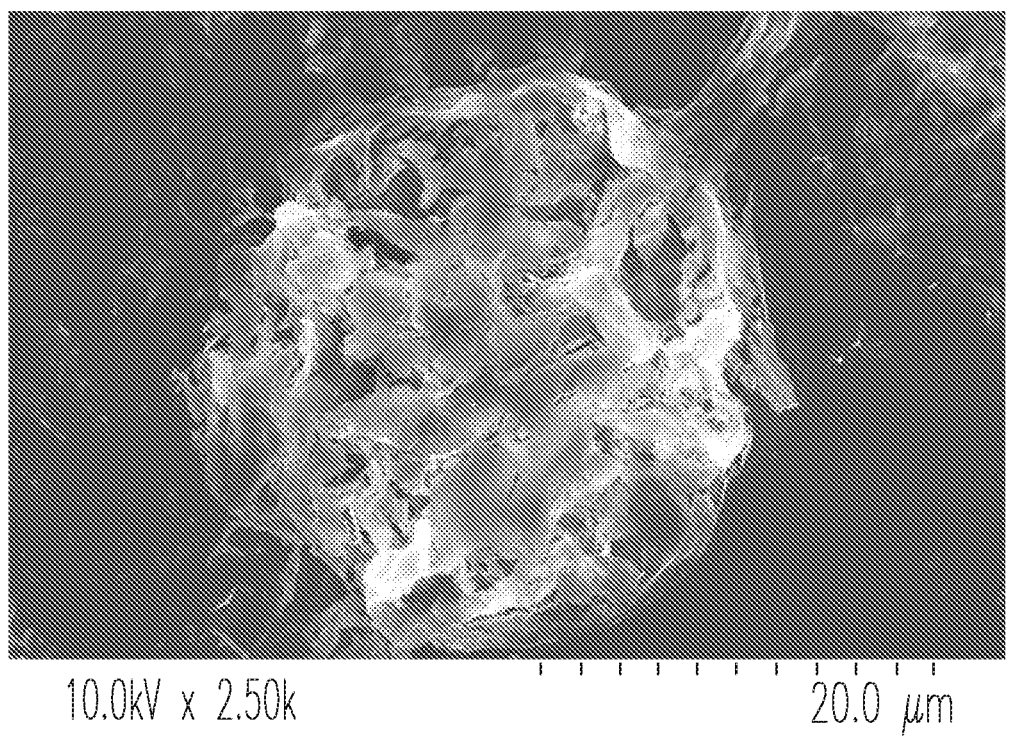
FIG. 8 is a scanning electron micrograph of one of the ultra-light weight hemostatic clay microparticles described herein after having partially reacted with blood.

FIGS. 7 and 8 are scanning electron micrographs of the clay microspheres described herein as they interact with blood and induce clotting. FIG. 7 shows unreacted microspheres (in bright contrast at the bottom left of the image in FIG. 7), as well as microspheres that have been saturated with blood (in darker contrast at the top of image in FIG. 7). FIG. 8 shows a close-up view of a clay microsphere that appears to have partially reacted with blood. As can be seen in FIG. 8, most of the pore space of the clay microsphere has been occupied by blood. Without wishing to be bound by any theory, the inventor believes that at least in some examples the clay microspheres carry a net negative charge and therefore activate factor XII to factor XIIa of the coagulation cascade in the presence of blood via a chemical mechanism. The inventor also believes that the clay microspheres initiate mechanisms that absorb water into the microsphere, which also facilitates the clotting cascade via a physical mechanism.

The highly porous structure of the clay microspheres made by the method described herein can also allow one or more additive materials to be loaded into or onto the clay microspheres to provide functions that enhance or supplement the clotting functionality of the microspheres. Examples of additives that can be loaded onto or into the clay microspheres includes, but is not limited to, one or more pharmaceutically-active compositions (such as antibiotics, antifungal agents, antimicrobial agents such as compounds containing silver or copper ions or combinations thereof, anti-inflammatory agents, analgesics, antihistamines, or compounds that promote or enhance wound healing such as one or more amino acids), compounds containing silver or copper ions or combinations thereof, amino acids, or hemostasis-promoting agents such as ascorbic acid, tranexamic acid, rutin, and thrombin.

In some examples, the clay microspheres can include one or more additives that are incorporated into the clay material of the microspheres themselves, and not necessarily as an additive that is loaded into the pores. One example of this type of additive is one or more amino acids or other therapeutic agents that are intercalated into the cationic interlayer of the clay material (e.g., the cationic interlayer of hectorite shown in FIG. 1), which as described above, can act as a wound-healing promoter. Another example of such an additive is a gallium ion, such as a trivalent gallium ion ($Ga^{3+}$), which the inventor believes can act as both a hemostatic agent and an antimicrobial agent. In an example, gallium ions are incorporated into the clay material via ion exchange with sodium or lithium ions in the cationic interlayer of the clay material.

The present disclosure also describes a powder composition comprising the clay microspheres described herein loaded with one or more of the additives described above. In some examples, the powder composition comprises a dry mixture comprising first clay microspheres loaded with one or more additives and second clay microspheres that are not loaded with additives (e.g., that have open pores). The amount of the first clay microspheres (e.g., additive-loaded microspheres) relative to the second clay microspheres (e.g., non-loaded microspheres) will depend on the intended use of the dry mixture composition. For example, if the intended use is a typical wound (e.g., one that is not expected to have much bleeding and that will clot relatively easily), than the composition might have a large portion of non-loaded clay microspheres and a small portion of additive-loaded microspheres (or even no additive-loaded microspheres). If the intended use is for a larger wound or of a patient who is expected to have clotting issues (e.g., a patient on one or more blood thinners), than the dry mixture composition can comprise a larger percentage of microspheres loaded with one or more hemostasis-promoting agents to improve the hemostasis ability of the composition. If the intended use is in a place where it is expected to be difficult to keep a sterile environment, than the dry mixture composition can include a larger percentage of microspheres loaded with one or more antimicrobial agents or one or more antibiotic agents. In this way, the specific recipe of the dry mixture composition (e.g., percentage of loaded or non-loaded microspheres and the specific type or types of additives loaded onto or into the loaded microspheres) can be formulated depending on the specifics of the particular application for which that dry mixture composition is being made.

A method of forming clay microspheres according to the present disclosure includes the steps of: (a) forming a suspension of the clay material that is being used to form the microspheres (e.g., hectorite); (b) forming small droplets of the clay suspension; (c) very shortly after step (b), freezing the small droplets of clay suspension to provide frozen clay droplets; and (d) freeze-drying the frozen clay droplets for a specified period of time to provide porous microparticles.

In an example, forming the suspension of clay material (Step (a)) comprises mixing a specified amount of the clay material, e.g., hectorite, into a suspending liquid, such as water, for example highly-pure water, such as an ultrapure deionized water. In an example, when clay materials like hectorite (e.g., that are formed from a plurality of small platelets such as the nanosized platelets that form hectorite) is mixed with the suspending liquid, the small platelets become dispersed in the suspending liquid to form a clear or substantially clear suspension. In an example, the small platelets that form the clay material comprise an anisotropic charge, which allows the small platelets to be randomly or substantially randomly dispersed in the suspending liquid. The concentration of the clay material in the suspension is selected to provide for the formation of microparticles having certain desired properties (such as a desired density, size, or porosity). In an example, the concentration of the clay material in the suspension is less than or equal to 2 wt. %, such as from about 1 wt. % to about 2 wt. %. In an example where hectorite is used to form the clay microspheres, commercially-available hectorite particles sold under the LAPONITE RD trade name (Rockwood Specialties Inc., Princeton, NJ, USA).

In an example, forming the suspension (Step (a)) includes adding the clay material to the suspending liquid under constant or substantially constant stirring for a specified period of time, such as at least 15 minutes, at least 20 minutes, at least 30 minutes, at least 45minutes, at least 60 minutes, or more. In an example, the stirring to form the suspension is performed at room temperature.

After forming the suspension, the method includes forming small droplets of the suspension (Step (b)). In an example, forming the small droplets (Step (b)) includes dripping the suspension onto an ultrasonic probe to produce the small droplets. However, other methods of forming the small droplets can be used including, but not limited to, spraying the suspension into the small droplets. In an example, the droplets of the solution suspension have a size (e.g., diameter) that is similar in scale to the size of the clay microspheres that result from the method, e.g., a size of from about 30 µm to about 200 µm, such as from about 50 µm to about 200 µm. In an example, the size of the droplets is selected to achieve a desired final size of the clay microspheres. Without wishing to be bound by any theory, the inventor believes that the process of freezing and then freeze drying the droplets can result in some expansion of size such that the final clay microspheres may be slightly larger than the size of the droplets that form them.

Shortly after forming the suspension droplets, and in some examples immediately after or even substantially simultaneously with the formation of the droplets, the method includes freezing the droplets to form frozen clay suspension droplets. In an example, the suspension droplets are frozen by placing them in an environment with a specified temperature of −100° C. or less, such as −150° C. or less, for example at about −196° C. (e.g., the temperature at which liquid nitrogen boils). In an example, the specified temperature can be achieved by using liquid nitrogen to freeze the clay suspension droplets.

In some examples, the steps of forming the suspension droplets (Step (b)) and freezing the suspension droplets (Step (c)) can be done substantially simultaneously, for example by spraying the clay suspension into a chamber that has been chilled to a sufficiently low temperature such that the suspending liquid of the suspension droplets will freeze very soon after being sprayed into the chamber, a process that can also be referred to as "freeze spraying."

After freezing (Step (c)), the method includes freeze-drying the frozen clay suspension droplets for a specified freeze-drying time (Step (d)), which drives off the liquid portion of the frozen clay suspension and results in a porous microparticle made from the clay material. In an example, the freeze-drying (Step (d)) includes collecting the frozen clay suspension droplets and placing them in a freeze-drying apparatus (also referred to simply as a "freeze dryer"), which is subjected to freeze-drying conditions (e.g., where the temperature and pressure experienced by the frozen suspension droplets are below the triple point of water (e.g., below about 0°° C. and about 610 Pa) for a specified period of time that is sufficient to sublimate all or nearly all of the water out of the droplets and leave behind the clay material that had been in the suspension. The specified freeze-drying time is selected so that all or substantially all of the suspending liquid from the suspension is dried out of the frozen droplets so that what is left behind is the clay material in a porous form. The specific parameters of the freeze drying (e.g., temperature and pressure within the freeze drying and the freeze-drying time selected) will depend on several factors, including the composition of the clay material used, the concentration of the clay material in the suspension, the size of the frozen suspension droplets, and the mass of frozen suspension droplets being dried in the freeze dryer. In an example, the specified freeze drying time is at least about 12 hours, for example at least about 24 hours, such as up to 48 hours or more.

The inventor has found that when the clay material is formed into small suspension droplets, e.g., by spraying the suspension to form small, and then very shortly after forming the suspension droplets freezing the suspension droplets, and then freeze-drying the frozen suspension droplets for a specified period of time results in microspheres having the highly porous three dimensional structure described above.

Figure 9:
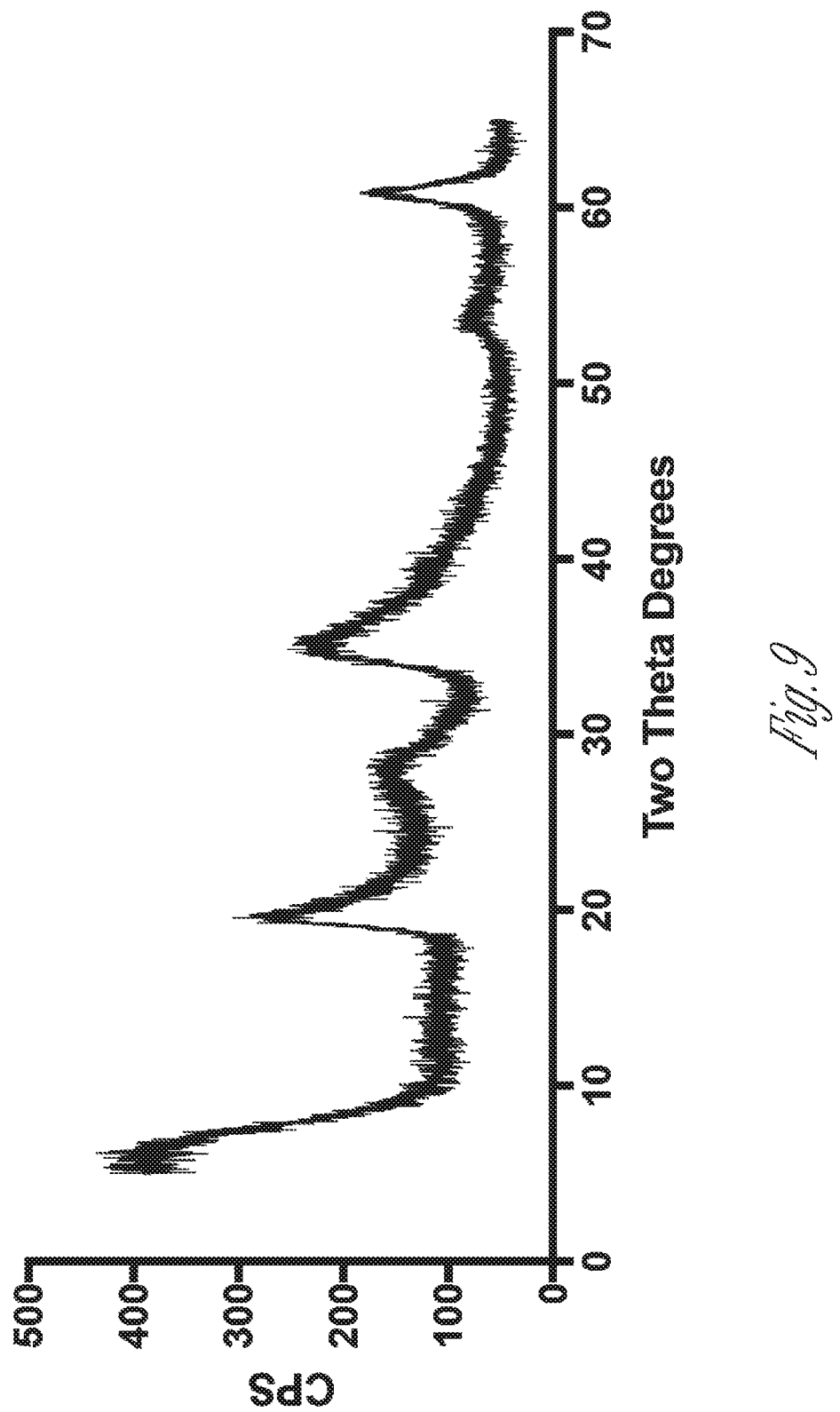
FIG. 9 is an X-Ray diffraction pattern graph of the ultra-light weight hemostatic clay microparticles described herein.

The method described above is able to produce relatively large quantities of the powdered clay microspheres and in a short period of time (e.g., the total time of production between preparing the clay suspension and the completion of freeze drying can be as little as 30 hours). X-ray diffraction analysis (FIG. 9) of microspheres made by freeze spraying and freeze drying a hectorite suspension confirmed that the resulting microspheres are composed of hectorite.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of producing a hemostatic composition, the method comprising:
    mixing a clay material comprising a crystalline hydrated form of a layered silicate within a suspending liquid for a specified period of time so that platelets of the clay material are sufficiently dispersed in the suspending liquid to form a clear or substantially clear clay suspension;
    spraying the clear or substantially clear clay suspension in order to form of droplets of the clear or substantially clear clay suspension having a diameter of less than or equal to about 250 micrometers, wherein the clear or substantially clear clay suspension is sprayed into an environment with a sufficiently low temperature to freeze the suspending liquid of the droplets to provide frozen droplets of the clear or substantially clear clay suspension; and freeze-drying at least a portion of the frozen droplets to provide a powder comprising hollow or highly-porous microspheres comprising the clay material, wherein the hollow or highly-porous microspheres have a sphere-like or substantially sphere-like shape, wherein the hollow or highly-porous microspheres have a diameter of from about 40micrometers to about 250 micrometers and comprise a porous structure with a plurality of pores formed in the microspheres, wherein each of the plurality of pores has a pore size of from about 1micrometer to about 10 micrometers, and wherein the powder exhibits hemostatic properties.

2. A method according to claim 1, wherein the liquid comprises water.

3. A method according to claim 1, wherein at least a portion of the platelets of the clay material in the clear or substantially clear clay suspension have an anisotropic charge.

4. A method according to claim 1, wherein a concentration of the clay material in the clear or substantially clear clay suspension is less than or equal to 2 wt. % of the clay solution.

5. A method according to claim 1, wherein the environment for the step of spraying the clear or substantially clear clay suspension is at a temperature of −100° C. or less.

6. A method according to claim 1, wherein the step of freeze-drying the frozen droplets comprises exposing the plurality of frozen droplets to an environment with a temperature below about 0° C. and an absolute pressure of less than about 610 Pa for a specified freeze-drying time.

7. A method according to claim 1, wherein the frozen droplets have a diameter of from about 30 micrometers to about 200micrometers prior to the freeze-drying.

8. A method according to claim 7, wherein the hollow or highly-porous microspheres have a diameter of from about 50 micrometers to about 200 micrometers.

9. A method according to claim 1, wherein the powder has a density, when uncompacted, of from about 0.006 grams per cubic centimeter to about 0.009 grams per cubic centimeter.

10. A method according to claim 1, wherein the clay material comprises hectorite, laponite, kaolinite, bentonite, montmorillonite, saponite, palygorskite, sepiolite, or a combination thereof.

11. A method according to claim 1, wherein the powder comprising-the-exhibits hemostatic properties with a ratio of 10 milligrams per 0.2 milliliters of blood or less.

12. A method according to claim 1, wherein the hollow or highly-porous microspheres have a specific surface area of at least about 75 square meters per gram.

13. A method according to claim 1, further comprising loading one or more additives into or onto at least a first portion of the hollow or highly-porous microspheres.

14. A method according to claim 13, further comprising mixing the first portion of the hollow or highly-porous microspheres with a second portion of the hollow or highly-porous microspheres, wherein the second portion of the hollow or highly-porous microspheres are not loaded with any additive.

15. A method according to claim 13, wherein the one or more additives comprise at least one of:
an amino-acid, an antibiotic agent, a pharmaceutically-active composition, an antifungal agent, an antimicrobial agent, an anti-inflammatory agent, an analgesic agent, an antihistamine agent, a hemostasis promoting agent, gelatin, collagen, silver ions, copper ions, gallium ions, or combinations thereof.

16. A method according to claim 1, wherein each of the plurality of pores of the hollow or highly-porous microspheres has a size of from about 3 micrometers to about 6 micrometers.

17. A method according to claim 1, wherein mixing the clay material within the suspending liquid comprises adding the clay material to the suspending liquid and constantly or substantially constantly stirring the suspending liquid for the specified period of time so that the platelets of the clay material are sufficiently dispersed in the suspending liquid to form the clear or substantially clear clay suspension.

18. A method according to claim 1, wherein the specified period of time is at least 30 minutes.

19. A method according to claim 1, wherein the specified period of time is at least 60 minutes.

* * * * *

UNITED STATES PATENT AND TRADEMARK OFFICE
CERTIFICATE OF CORRECTION

| | |
|---|---|
| PATENT NO. | : 12,296,064 B2 |
| APPLICATION NO. | : 17/276396 |
| DATED | : May 13, 2025 |
| INVENTOR(S) | : Isabelle Denry |

It is certified that error appears in the above-identified patent and that said Letters Patent is hereby corrected as shown below:

In the Specification

In Column 3, Line 60, delete "250" and insert --250 µm,-- therefor

In Column 3, Line 61, delete "200" and insert --200 µm.-- therefor

In Column 3, Line 62, delete "200" and insert --200 µm,-- therefor

In Column 3, Line 64, delete "200" and insert --200 µm.-- therefor

In Column 7, Line 16, delete "liquid ," and insert --liquid,-- therefor

In Column 7, Line 36, after "Inc.,", delete a linebreak

In Column 7, Line 42, delete "45minutes," and insert --45 minutes,-- therefor

In Column 7, Line 52, before "suspension", delete "solution"

In the Claims

In Column 10, Line 11, Claim 1, after "form", delete "of"

In Column 10, Line 26, Claim 1, delete "40micrometers" and insert --40 micrometers-- therefor In Column 10, Line 30, Claim 1, delete "1micrometer" and insert --1 micrometer-- therefor In Column 10, Line 53, Claim 7, delete "200micrometers" and insert --200 micrometers-- therefor Signed and Sealed this
Second Day of September, 2025

Coke Morgan Stewart
*Acting Director of the United States Patent and Trademark Office*

In Column 10, Line 66, Claim 11, delete "comprising-the-exhibits" and insert --exhibits-- therefor In Column 12, Line 6, Claim 16, delete "6micrometers." and insert --6 micrometers.-- therefor